United States Patent [19]

Byrne et al.

[11] Patent Number: 5,252,471
[45] Date of Patent: Oct. 12, 1993

[54] DIRECTED BIOSYNTHESIS OF CHOLESTEROL LOWERING COMPOUNDS

[75] Inventors: Kevin M. Byrne, West Trenton, N.J.; Louis Kaplan, New York City, N.Y.; Mary N. Omstead, Gladstone, N.J.

[73] Assignee: Merck & Co., Inc., Rahway, N.J.

[21] Appl. No.: 848,573

[22] Filed: Mar. 9, 1992

[51] Int. Cl.$^5$ .......................... C12P 17/18; C12N 1/14
[52] U.S. Cl. .................................. 435/119; 435/254.1
[58] Field of Search ........................ 435/119, 254, 911

[56] References Cited

FOREIGN PATENT DOCUMENTS

| | | |
|---|---|---|
| 0448393 | 9/1991 | European Pat. Off. |
| 0450812A1 | 10/1991 | European Pat. Off. |
| 0494622A1 | 7/1992 | European Pat. Off. |
| 0503520 | 9/1992 | European Pat. Off. |

OTHER PUBLICATIONS

Baxter et al., Squalestatin 1, A Potent Inhibitor of Squalene Synthase Which Lowers Serum Cholesterol in Vivo, J. Biol. Chem., vol. 267, pp. 11705-11708 (1992).

Primary Examiner—Douglas W. Robinson
Assistant Examiner—Jeffrey J. Sevigny
Attorney, Agent, or Firm—Catherine A. Dolan; Melvin Winokur; Joseph F. DiPrima

[57] ABSTRACT

Compounds of Structural Formula (I)

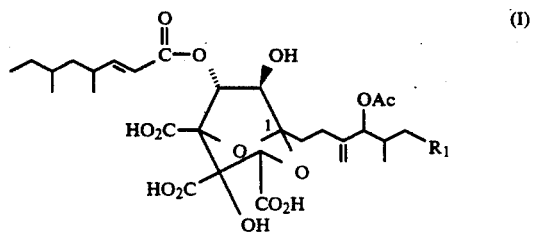

are produced by directed biosynthesis. These compounds are squalene synthetase inhibitors useful as cholesterol-lowering agents.

8 Claims, 1 Drawing Sheet

DIRECTED BIOSYNTHESIS OF CHOLESTEROL LOWERING COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorus containing inhibitors of squalene synthetase have been isolated as natural products. These natural product inhibitors are described in U.S. Pat. Nos. 5,053,425; 5,055,487 and 5,026,554.

U.S. Pat. No. 5,053,425 discloses a zaragozic acid compound of structure

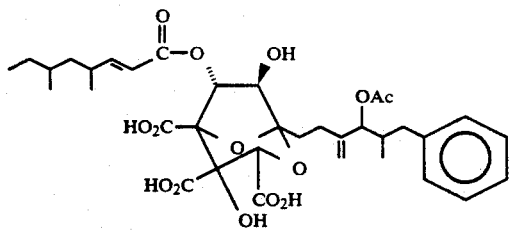

hereafter referred to as zaragozic acid A. Applicants have now found that providing certain aryl, heteroaryl, aralkyl or heteroaralkyl carboxylic acids to a culture that produces zaragozic acid A leads to the incorporation of an aryl or heteroaryl moiety into the C-1 side chain of zaragozic acid A. The products of this directed biosynthesis are also useful as squalene synthetase inhibitors.

DETAILED DESCRIPTION OF THE INVENTION

Figure 1:
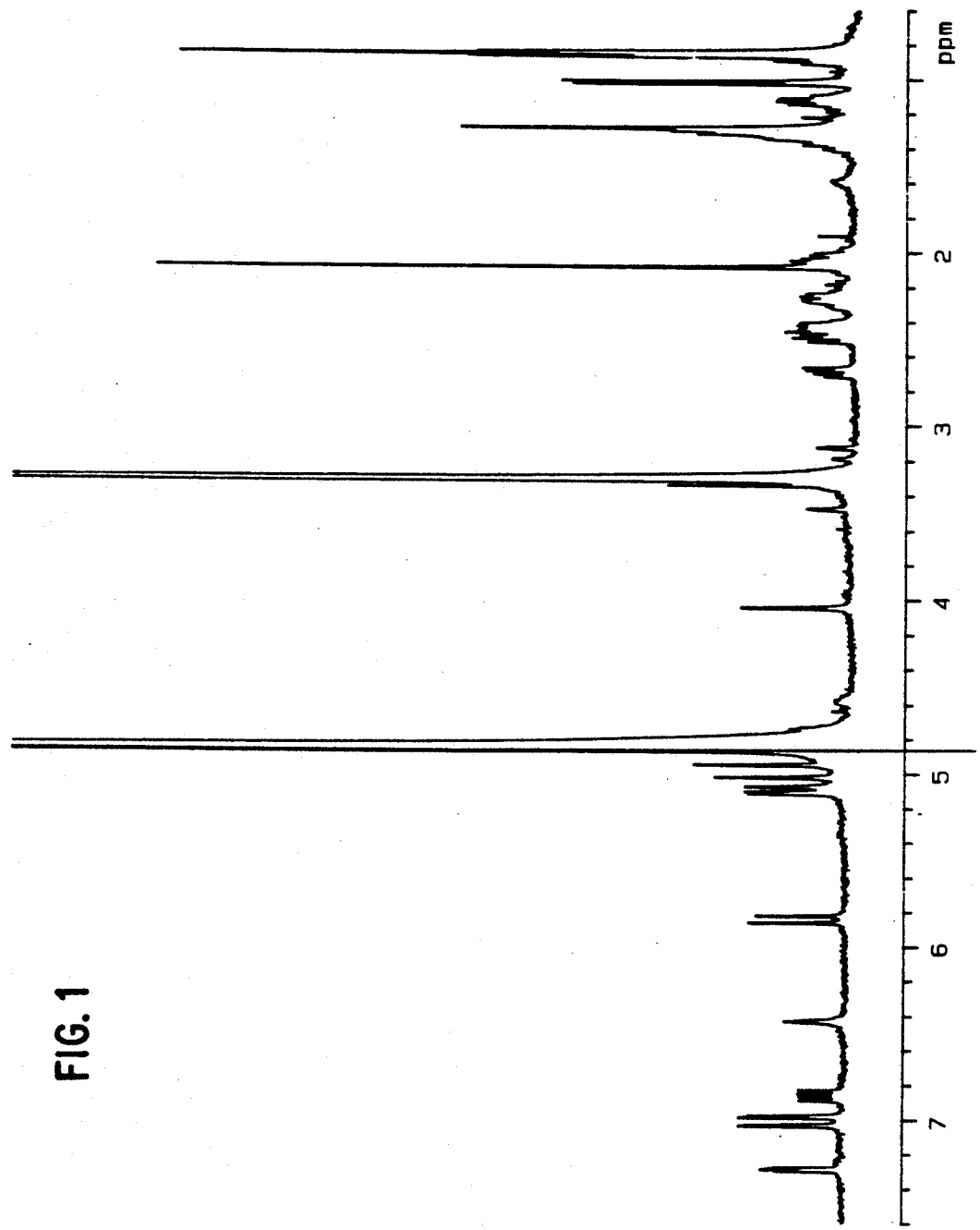

The present invention is directed to a process for the formation of a compound of structural formula (I):

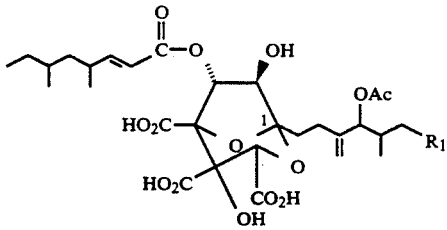

comprising the addition of a compound of formula (II) selected from the group consisting of:
(a) $R_1$—$CO_2H$; and
(b) $R_1$—$CH_2$—$CHNH_2CO_2H$;
wherein $R_1$ is selected from

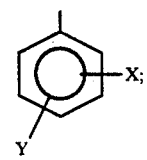  (a)

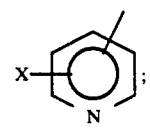  (b)

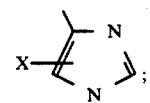  (c)

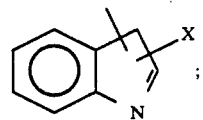  (d)

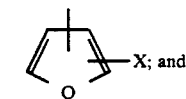  (e)

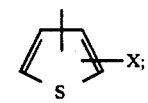  (f)

and wherein X and Y are selected from the group consisting of:
(a) H;
(b) halogen (F, Cl, Br, I);
(c) OH; and
(d) $CH_3$;
to a zaragozic acid A producing culture and isolating the product (I) from the culture broth.

In one embodiment of the present invention the zaragozic acid A producing culture is selected from the group consisting of:
(a) MF5453 (ATCC 20986),
(b) MF5565 (ATCC 74068),
(c) MF5599 (ATCC 74065),
(d) MF5572 (ATCC 74066), and
(e) MF5573 (ATCC 74067), or a mutant having essentially the same characteristics as one of the above.

In one class of this embodiment $R_1$ is selected from

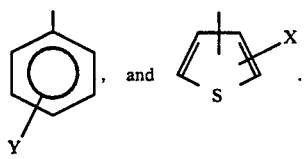

Exemplifying this class is the process wherein X is H and Y is OH, and the microorganism is MF5453.

The culture MF5453 is that of a fungus isolated from a water sample obtained from the Jalon River, Zaragoza, Spain. This culture has been deposited with the American Type Culture Collection at 12301 Parklawn Drive, Rockville, Md. 20852 as ATCC 20986. The microorganism MF5453, its morphological characteristics and a fermentation procedure using this microorganism have been described in U.S. Pat. No. 5,053,425.

The culture MF5565 is a strain of *Exserohilum rostratum*, which was isolated from bark of *Theobroma cacao* (Philippines). The culture has been deposited with the ATCC as ATCC 74068. The microorganism MF5565, its morphological characteristics and a fermentation procedure using this microorganism have been described in U.S. patent application Ser. No. 722,049 filed Jun. 27, 1991.

This strain, MF5565, was recovered from the bark of *Theobroma cacao*, collected in Los Banos, Laguna Province, Philippines. Bark discs were removed with a leather punch (no. 245, C.S. Osborne & Co., Harrison, N.J.). Discs were approximately 1 cm in diameter and 0.3-1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar medium (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to one month for the development of fungal colonies on bark discs and the agar.

Strain MF5565 exhibits the following morphological characteristics.

Colonies relatively fast-growing, in 1 week attaining a diameter of: 50 mm on cornmeal agar (Difco Laboratories); 50-52 mm on yeast-malt extract agar (10 g malt extract, 2 g yeast extract, 20 g agar in 1 L distilled water); 60 mm on V8 juice agar (200 mL V8 juice, Campbell Soup Co., 3 g CaCO$_3$, 20 g agar diluted to 1 L distilled water). On yeast-malt agar with both submerged and aerial mucelium, with submerged mycelium sometimes forming radial strands, floccose to cottony or lanose in age, with margin appressed, minutely fimbriate to even, hyaline to pale gray at the margin but soon darkening to dark gray or dark olive-gray, or black in age, Dark Olive-Gray, Iron Gray, Dark Mouse Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions. Odors, sclerotia, stromata, or pseudothecia absent. Conidiophores arising from uppermost aerial mycelium, up to 600 μm long, 3-4.5 μm wide, straight or flexuous, with geniculate apices, with walls smooth, or occasionally finely incrusted, usually bearing 2-10 conidia, pale olive-gray to olive-gray. Conidiogenous cells polytretic, integrated, sympodial, indeterminate, terminal or intercalary, with slightly raised, darkened scars surrounding a minute pore at the conidiogenous locus. Conidia 45-250×7-20 μm, , mostly 75-180 μm long, variable in shape, broadly ellipsoidal, fusoid, obclavate, or tapered cylindrical, straight to curved, or rarely sigmoid, with broadly rounded apices, smooth, 5-22 septate, with basal septum most thickened and darkened, with terminal septum often also darker than septa delimiting central cells, with a distinct cylindrical hilar appendix protruding 1-2.5 μm, pedicel-like extensions absent, initially germinating from apical and basal cells pale gray to olive-gray in 3% KOH. Hyphae septate, branched, pale olive-gray to olive-brown, usually smooth, but occasionally with fine incrustations.

Strain MF5565 belongs to the genus *Exserohilum rostratum* based on the combination of polytretic conidiogenous cells that give rise to predominately multiseptate, dematiaceous phragmoconidia. The basal cell of the conidium is delimited by a thick, darkened septum, and has a protruding hilar appendix. Strain MF5565 is identified as *Exserohilum rostratum* based on the predominance of straight and curved conidia, darkened septa delimiting both the basal and terminal cells, and relatively long conidia (A. Sivanesan. 1987 Graminicolous species of Bipolaris, Curvularia, Drechslera, Exserohilum and their telemorphs. CMI Mycological Paper No. 158).

The culture MF5599, is a strain of *Curvularia lunata* var. *aeria* isolated from bark of *Ficus elastica* (Diliman, Quezon City, Philippines). The culture has been deposited with the ATCC as ATCC 74065. The microorganism MF5599 has the same morphological characteristics as MF5572, described below.

The culture MF5572 is a strain of *Curvularia lunata* var. *aeria,* isolated from tree bark (Philippines). This culture has been deposited with the ATCC as ATCC 74066. The microorganism MF5572, its morphological characteristics and a fermentation procedure using this microorganism have been described in U.S. patent application Ser. No. 715,535 filed Jun. 14, 1991.

Strain MF5572, was recovered from the bark of an unidentified tree, collected in Diliman, Quezon City, Philippines. Bark discs were removed with a leather punch (no. 245, C.S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5572 has been identified as *Curvularia lunata* var. *aeria* and exhibit the following morphological characteristics.

Colonies are relatively fast-growing, in 1 week attaining a diameter of: 30-35 mm on cornmeal agar (Difco Laboratories); 30-35 mm on yeast-malt extract agar (10 g malt extract, 2 g yeast extract, 20 g agar in 1 L distilled water); 40-55 mm on V8 juice agar (200 mL V8 juice, Campbell Soup Co., 3 g $CaCO_3$, 20 g agar diluted to 1 L distilled water). On yeast-malt agar both submerged and aerial mycelia form, are slightly raised in side view, velvety to floccose when young, cottony or lanose in age, with margin slightly raised, even to wavy, hyaline to pale gray at the margin but soon darkening to grayish olive, gray, to dark olive-gray, Smoke Gray, Light Grayish Olive, Deep Olive-Gray, Dark Olive-Gray, Iron Gray, Castor Gray (capitalized color names from Ridgway, R. 1912. Color Standards and Nomenclature, Washington, D.C.), in reverse yellowish gray towards the margin but soon olivaceous gray, in age developing dark olive-black spots and patches in the agar, often with patches or tufts of hyaline to pale gray aerial hyphae developing in older portions, odors and pseudothecia absent. The surface of cultures in excess of 3 weeks old, generally develop straight to curved, cylindrical, finger-like stromata, 0.5-1 mm tall, which project upward from the oldest regions of the colony surface. Stromata formation is best on nutrient-rich media, e.g. potato-dextrose agar, oatmeal agar, or glucose- yeast-malt extract agar.

Conidiophores arising from aerial hyphae, 30-200-×3-5 μm, septate, straight or flexuous, sometimes branched in age, with apices straight, curved or geniculate, smooth, thin- to slightly thick-walled, olive-brown to olive-gray in 3% KOH, bearing 2-10 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 18-28×9-14 μm, consistently 3-septate, broadly elliptical, with penultimate, distal cell curved and distinctly swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched. Stromatic tissue a textura intricata, with cells hyaline in 3% KOH.

The culture MF5573, *Curvularia lunata* var. *lunata*, was isolated from *Ficus elastica* tree bark (Philippines). The culture has been deposited with the ATCC as ATCC 74067. The microorganism MF5573, its morphological characteristics and a fermentation procedure using this microorganism have been described in U.S. patent application Ser. No. 715,535 filed Jun. 14, 1991.

*Curvularia lunata* var. *lunata* MF5573 was recovered from the bark of *Ficus 380 elastica* collected in Diliman, Quezon City, Philippines. Bark discs were removed with a leather punch (no. 245, C.S. Osborne & Co., Harrison, N.J.). Discs were approximately 1 cm in diameter and 0.3-1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycliiie, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5573 has been identified as *Curvularia lunata* var. *lunata* and exhibits the following morphological characteristics.

Colonies are relatively fast-growing, in 1 week attaining a diameter of: 35-40 mm on cornmeal agar (Difco Laboratories); 40 mm on yeast-malt extract agar (10 g malt extract, 2 g yeast extract, 20 g agar in 1 L distilled water); 45-50 mm on V8 juice agar (200 mL V8 juice, Campbell Soup Co., 3 g $CaCO_3$, 20 g agar diluted to 1 L distilled water). On yeast-malt agar both submerged and aerial mycelia form, with aerial mycelia sometimes forming radial strands, floccose to cottony or lanose in age, with margin appressed, minutely fimbriate, hyaline to pale gray at the margin but soon darkening to dark gray or dark olive-gray, Castor Gray, Dark Olive-Gray, Iron Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions, occasionally forming pale gray to hyaline sectors, odors, sclerotia, stromata, or pseudothecia absent.

Conidiophores arising from surface or aerial hyphae, 15-250×3-5 μm, septate, straight or flexuous, sometimes branched in age, with apices straight, curved or geniculate, smooth, thin- to slightly thick-walled, olive-brown to olive-gray in 3% KOH, bearing 4-15 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 21-30×9-13.5 μm, usually 3-septate, infrequently 4-septate, broadly elliptical, with penultimate, distal cell curved and often obliquely swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched.

Vegetative cells of a culture capable of producing zaragozic acids, such as: MF5453 (ATCC 20986); MF5565 (ATCC 74068); MF5599 (ATCC 74065); MF5572 (ATCC 74066); or MF5573 (ATCC 74067) can be obtained by culturing the microorganism in an aqueous nutrient medium containing sources of assimilable carbon and nitrogen, preferably under aerobic conditions. Nutrient media may also optionally contain mineral salts, high molecular weight polyanions (CARBOPOL ®, JUNLON ®), and/or defoaming agents.

The preferred sources of carbon in the nutrient medium are carbohydrates such as glucose, glycerin, and the like. Other sources which may be included are maltose, fructose, sucrose, and the like. In addition, complex nutrient sources such as oat flour, may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, and the like, as well as complex sources such as yeast extracts (hydrolysates, autolysates), dried yeast, tomato paste, peptone, corn steep liquor, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 20 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like.

The preferred process for production of these vegetative cells consists of inoculating spores or mycelia of the producing organism into a suitable medium and then cultivating tinder aerobic condition. After inoculation, the flasks are incubated with agitation at temperature ranging from 20° to 30° C., preferably 24° to 27° C. Agitation rates may range up to 400 rpm, preferably 200 to 240 rpm. Flasks are incubated over a period of 2 to 10 days, preferably 2 to 4 days. When growth is plentiful, the culture is ready to be washed, homogenized, and used in directed biosynthetic studies.

In addition, the compounds of the present invention may be more selectively synthesized by inhibiting the enzyme phenylalanine ammonia lyase (PAL) which is the first step in the degradation of L-phenylalanine to form benzoic acid. Benzoic acid has been shown to be the direct precursor of the aromatic ring system on the C-1 side chain of zaragozic acid A. Inhibitors of PAL include phenylpropiolic acid, D-phenylalanine, aminooxyacetic acid, p-coumaric acid, caffeic acid, D,L-$\beta$-phenylserine and D,L-2-hydroxyphenylalanine.

Furthermore, the process of the present invention may be carried out using a mutant for the parent strain that is lacking the PAL enzyme, resulting in a culture whose synthesis of the zaragozic acid is dependent on an exogenous source of benzoic acid. This culture more readily incorporates the compounds of Formula (II) because these compounds are not competing with an endogenous source of benzoic acid.

After growth, cells are harvested by filtration or centrifugation. To obtain a uniform suspension, the cell mixture is then homogenized using a homogenizer such as a hand-held BIOHOMOGENIZER TM (Bartlesville, Okla.) until no clumps or mycelial balls are visible (about 20 to 60 seconds).

Alternatively, the vegetative cells may be grown in media containing polyanions to give more beaded and grainy growth, which may eliminate the benefits of the homogenization step which transforms large balled growth to more disperse hyphal fragments.

After growth or the optional homogenization step, the cells are washed with distilled water or an aqueous buffer and resuspended in a medium consisting of 1 to 5% of a carbon/energy source such as glucose, glycerol, sucrose or the like and an appropriate buffer such as 5-10 mM PIPES (piperazine-N,N'-bis-[2-ethanesulfonic acid]), MOPS (3-[N-morpholino]-propanesulfonic acid), MES (2-[N-morpholino]ethanesulfonic acid), MOPSO (3-[N-morpholino]-2-hydroxypropanesulfonic acid), ACES (N-[2-acetamido]-2-aminoethanesulfonic acid), ADA (N-[2-acetamido]-2-iminodiacetic acid), BES (N,N-bis[2-hydroxyethyl]-2-aminoethanesulfonic acid), phosphate or the like to keep the pH less than 8, preferably pH 6 to pH 6.5. In order to guarantee uniform suspension of the cells, the container holding the cells is shaken vigorously.

Aliquots of the suspended cells are removed and are incubated at 20° to 30° C. for 24 to 144 hours with or without agitation, preferably at 25° C. for 120 hours with agitation. After this initial incubation, a compound of Formula (II) selected from $R_1$-$CO_2H$ and $R_1$—$CH_2$—$CHNH_2CO_2H$ wherein $R_1$ is as defined above is added, either as a free acid or as a biologically acceptable salt form such as sodium to a final concentration of 0.01 mM to 100 mM, preferably 0.25 to 0.5 mM, followed by additional incubation of 48 to 120 hours. After the additional incubation, the biosynthesis is terminated by the addition of a solvent such as methanol or acetonitrile, preferably methanol, and the broth is clarified.

In order to make the cells more permeable to the uptake of the compounds of Formula (II), the cells may be treated with toluene by adding 1-2 drops of toluene to the aliquot of cells after the initial incubation. The suspension is vigorously shaken at ambient temperature for 30 seconds, followed by the addition of a compound of Formula II to the suspension of cells and the additional incubation as described above.

The desired compounds of Formula (I) are extracted with solvent and purified by various chromatographic techniques such as silica gel, reverse phase and ion exchange. Preferably the compounds of Formula (I) are isolated by anion exchange chromatography followed by preparative reverse-phase high pressure liquid chromatography.

The following examples illustrate the formation of a compound of Formula (I).

EXAMPLE 1

A Compound of Formula (I) wherein $R_1$ is 3-thiophene

I. Directed Biosynthesis

Culture MF5453 was grown for 72 hours at 25° C. in KF medium (U.S. Pat. No. 5,053,425) and the cells harvested by centrifugation. The cells were washed (X2) with distilled water and resuspended to the original broth volume in 20 mM piperazine-N,N'-bis[2-ethanesulfonic acid](PIPES) buffer (pH 6.1) containing 3% sucrose. Five mL aliquots of this suspension were transferred to four 50 mL Erlenmeyer flasks and these flasks incubated at 25° C. with agitation. After 24 hours incubation, 3-thiophenecarboxylic acid (Na-salt) was added to a final concentration of 0.25 nM, 0.5 mM and 1.0 MM to each of three flasks, the fourth being a control. After an additional 96 hours incubation, the biosynthesis was terminated with the addition of two volumes of methanol and the broths clarified. The broth-methanol mixture was adjusted to pH 4.5 with formic acid, and the contents of the three flasks containing 3-thiophene-carboxylic acid were combined. The resulting mixture was applied to a 1 mL column of BIO-RAD® AG4X4 ion exchange resin in the formate cycle. The column was washed successively with 15 mL of MeOH-formate buffer (1/1 v/v; 50 mM formate adjusted to pH 4.5) and 15 mL of 60/40 MeCN/water (v/v). The column was then eluted with 15 mL of 60/40 MeCN/water containing 1 mL concentrated formic acid.

II. Isolation and Purification

Fifteen mL of AG4X4 eluate was reduced under nitrogen to 8 mL. The crude extract was filtered and 2 mL injected onto a BECKMAN® preparative HPLC (9.6 mm×250 mm) ODS column. The column was developed at 3.0 ml/min using a 35 minute linear gradient of 40% to 80% acetonitrile in water containing 0.1% $H_3PO_4$. Detection was at 215 nm. Peaks with an elution time of 28.9 minutes were collected and pooled. The pooled material was diluted with four volumes of deionized water and applied to a water-equilibrated $C_{18}$ SPE column. After washing with five volumes of deionized water, the column was dried with nitrogen, then eluted with methanol. The eluate was evaporated to dryness to yield a substance identified as the title compound. The $_1$H NMR of the title compound is shown in FIG. 1.

What is claimed is:

1. A process for the preparation of a compound of formula (I)

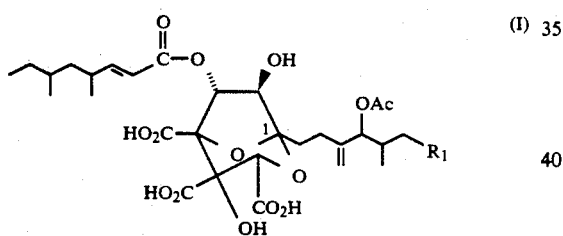
(I)

comprising adding a compound selected from the group consisting of:

(II) $R_1$—$CO_2H$; and
(III) $R_1$—$CH_2$—$CHNH_2CO_2H$;

wherein $R_1$ is selected from:

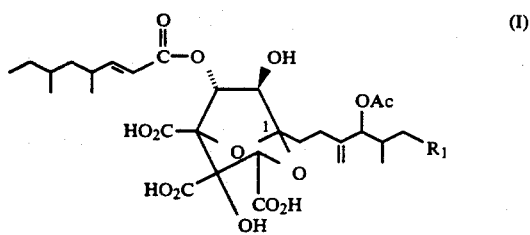
(I)

and wherein X and Y are selected from the group consisting of:

(a) H;
(b) halogen (F, Cl, Br, L);
(c) OH; and
(d) $CH_3$;

at a concentration of 0.01 nM to 100 nM
(a) MF5453; to a zaragozic acid A producing culture selected from the group consisting of:
(a) MF5453;
(b) *Exserohilum rostratum* (MF5565)
(c) *Curvularia lunata* var. *aeria* (MF5599)
(d) *Curvularia lunata* var. *aeria* (MF5572)
(e) *Curvularia lunata* var. *aeria* (MF5573)

or a mutant thereof and incubating for 48 to 120 hours at 20° to 30° C. at a pH less than 8 and isolating the product of formula (I) from the culture broth.

2. The process of claim 1 wherein $R_1$ is selected from the group consisting of:

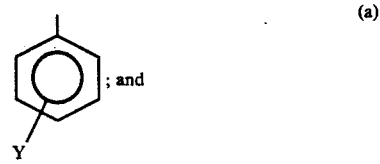
(a)

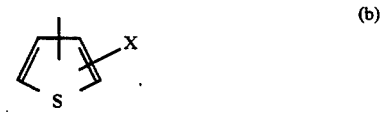
(b)

3. The process of claim 2 wherein $R_1$ is

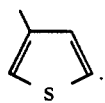

4. The process of claim 2 wherein $R_1$ is

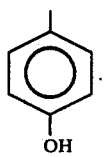

5. The process of claim 1 wherein an inhibitor of phenylalanine ammonium lyase is added to the culture broth.

6. The process of claim 1 wherein the cells of the zaragozic acid A producing culture are homogenized before the addition of the compound of Formula (II) (III) or (IV).

7. The process of claim 1 wherein the cells of the zaragozic acid A producing culture are treated with toluene before the addition of compound of Formula (II) or (III).

8. The process of claim 1 wherein the cells of the zaragozic acid a producing culture are washed after growth and resuspended in an aqueous medium before the addition of compound of Formula (II) or (III).

* * * * *